US011609565B2

(12) United States Patent
Abu Elreich

(10) Patent No.: US 11,609,565 B2
(45) Date of Patent: Mar. 21, 2023

(54) METHODS AND SYSTEMS TO FACILITATE MONITORING CENTER FOR RIDE SHARE AND SAFE TESTING METHOD BASED FOR SELFDRIVING CARS TO REDUCE THE FALSE CALL BY DEUDDACTION SYSTEMS BASED ON DEEP LEARNING MACHINE

(71) Applicant: Ahmad Hassan Abu Elreich, Fresno, CA (US)

(72) Inventor: Ahmad Hassan Abu Elreich, Fresno, CA (US)

(*) Notice: Subject to any disclaimer, the term of this patent is extended or adjusted under 35 U.S.C. 154(b) by 550 days.

(21) Appl. No.: 16/594,008

(22) Filed: Oct. 5, 2019

(65) Prior Publication Data

US 2020/0209850 A1 Jul. 2, 2020

Related U.S. Application Data

(60) Provisional application No. 62/742,146, filed on Oct. 5, 2018.

(51) Int. Cl.
*G05D 1/00* (2006.01)
*B60R 11/02* (2006.01)
(Continued)

(52) U.S. Cl.
CPC ........ *G05D 1/0061* (2013.01); *B60R 11/0241* (2013.01); *B60W 60/0051* (2020.02); *G05B 13/027* (2013.01); *G06Q 50/265* (2013.01); *G06Q 50/30* (2013.01); *G06V 20/597* (2022.01); *G10L 15/22* (2013.01); *G16H 40/67* (2018.01); *H04W 4/14* (2013.01); *B60R 2011/008* (2013.01); *B60R 2011/0026* (2013.01); *B60W 2420/42* (2013.01); *B60W 2540/221* (2020.02);
(Continued)

(58) Field of Classification Search
CPC ........ H04W 4/90; H04B 13/005; G06F 3/012; G06F 3/16; G06F 3/0233; G06F 1/163; H04L 29/06; H04M 11/00; A63F 13/87; G05D 1/0061; G08B 6/00
See application file for complete search history.

(56) References Cited

U.S. PATENT DOCUMENTS

| 9,019,131 B2 * | 4/2015 | Kim | H04B 13/005 |
| | | | 341/26 |
| 2008/0148030 A1 * | 6/2008 | Goffin | H04M 1/72448 |
| | | | 713/1 |

(Continued)

FOREIGN PATENT DOCUMENTS

| CN | 104580147 A | * | 4/2015 | ............. | H04L 29/06 |
| JP | 2004080653 A | * | 3/2004 | ............. | H04M 11/00 |

(Continued)

*Primary Examiner* — Yuri Kan

(57) ABSTRACT

A method and system to facilitate monitoring of vehicles, riders, and drivers that includes receiving, using a communication device, and input related to driver energy and driver availability from one or more driver devices. Further, the method may include a step of analyzing, using a processing device, the input related to driver energy to determine energy levels of the one or more drivers. Further, the method may include matching, using the processing device, the rider with a driver based on the analyzing. Further, the method may include transmitting, using the communication device, a notification to the rider device and a matched driver device.

1 Claim, 9 Drawing Sheets

(51) Int. Cl.
   *G06Q 50/30*       (2012.01)
   *G06Q 50/26*       (2012.01)
   *G16H 40/67*       (2018.01)
   *G05B 13/02*       (2006.01)
   *G10L 15/22*       (2006.01)
   *H04W 4/14*        (2009.01)
   *B60W 60/00*       (2020.01)
   *G06V 20/59*       (2022.01)
   *B60R 11/00*       (2006.01)

(52) U.S. Cl.
   CPC ... *B60W 2540/229* (2020.02); *B60W 2556/45* (2020.02); *G10L 2015/223* (2013.01)

(56) References Cited

U.S. PATENT DOCUMENTS

| | | | |
|---|---|---|---|
| 2009/0312817 A1* | 12/2009 | Hogle | A61B 5/682 607/54 |
| 2010/0238005 A1* | 9/2010 | White | G08B 6/00 340/407.2 |
| 2014/0129843 A1* | 5/2014 | Shi | G06F 21/32 713/182 |
| 2015/0290454 A1* | 10/2015 | Tyler | G06F 3/012 607/134 |
| 2016/0055758 A1* | 2/2016 | Francis | G09B 7/00 434/236 |
| 2017/0168625 A1* | 6/2017 | Shin | G06F 1/1652 |

FOREIGN PATENT DOCUMENTS

| | | | | |
|---|---|---|---|---|
| JP | 2016076202 A | * | 5/2016 | ............. G06F 1/163 |
| KR | 20150054560 A | * | 5/2015 | ........... G06F 3/0233 |
| KR | 20160089724 A | * | 7/2016 | ................ G06F 3/16 |
| KR | 101861128 B1 | * | 5/2018 | ............. A63F 13/87 |

* cited by examiner

METHODS AND SYSTEMS TO FACILITATE MONITORING CENTER FOR RIDE SHARE AND SAFE TESTING METHOD BASED FOR SELFDRIVING CARS TO REDUCE THE FALSE CALL BY DEUDDACTION SYSTEMS BASED ON DEEP LEARNING MACHINE

FIELD OF THE INVENTION

The present disclosure relates generally to the field of data processing. More specifically, the present disclosure describes methods and systems to facilitate monitoring of vehicles, riders, drivers and self driving cars.

BACKGROUND OF THE INVENTION

Ride sharing services are good examples of scenarios where a driver may have to make multiple decisions and may be distracted as the driver may be obstructed by looking at app, riders, requests, and so on. Therefore, the driver may make a lot of wrong decisions.

Further, drivers may be drowsy, or may be tired after continually driving for extended periods of time. However, the drivers may still get long rides irrespective of tiredness and energy level. Also, you never know when driver gets sleepy 6:00 pm or 6:00 am. Also a driver may get sleepy and drowsy while he or she providing a trip just half way to drop the ridder to destination which we provide solution.

Drivers and Riders may need to have silent communication with monitoring center for emergency like silent panic alarm or to avoid been shy to ask the driver to slow down or the driver is shy to ask the riders to not too be loud. Also system can alert us with the stress or fright feelings of Rider or driver and have silent communication through textile or fabric smart network.

Further, even self-driving vehicles so far make false calls deductions, and wrong decisions which delay the technology. In fact self driving cars may need decades with the available technology to have safe self driving cars because of the hidden false calls by he cars. there is may a need to transfer the available cars to smart cars with remote-self driving technology portable kits provided by testing self driving automakers. This self driving can be tested connected at virtual mode, also can be tested under remotely driving the car from station center under the supervision of driver, remotely driver and research and development stuff to be the safest and will be the fastest.

Therefore there a need for improved methods and systems to facilitate monitoring of vehicles, riders, and drivers that may overcome one or more of the above-mentioned problems and/or limitations.

SUMMARY

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

According to some embodiments, a method to allow a rider to book a ride in a ride-sharing service based on an energy level of a driver is disclosed. Accordingly, the method may include a step of receiving, using a communication device, input related to a ride from a rider device. Further, the method may include receiving, using the communication device, input related to driver energy and driver availability from one or more driver devices. Further, the method may include a step of analyzing, using a processing device, the input related to driver energy to determine energy levels of the one or more drivers. Further, the method may include matching, using the processing device, the rider with a driver based on the analyzing. Further, the method may include transmitting, using the communication device, a notification to the rider device and a matched driver device.

Further, according to some embodiments, a method to facilitate driver safety while driving a vehicle by determining driver energy level, distractions, and/or one or more obstacles is disclosed. Further, the method may include a step of analyzing, using a processing device, the input related to the vehicle to detect a driver energy level, distraction, or potential obstacles. Further, the method may include a step of transmitting, using the communication device, a notification to the one or more driver devices about energy level, distraction, or one or more obstacles.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and subcombinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

DETAIL DESCRIPTIONS OF THE INVENTION

Figure 1:
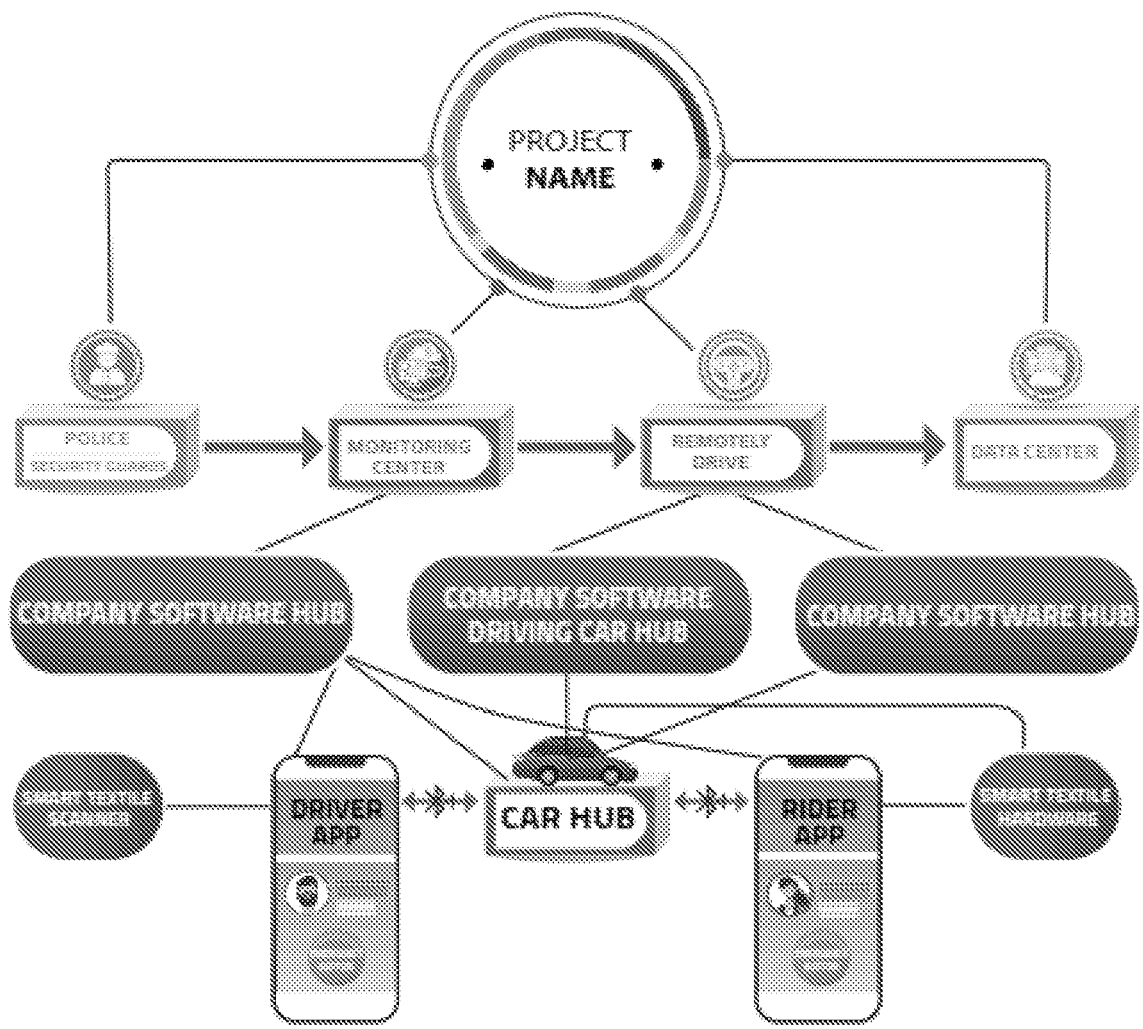
FIG. 1 is an illustration of an online platform consistent with various embodiments of the present disclosure, illustrating driver and rider software application connections.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of monitoring of vehicles, riders, and drivers, embodiments of the present disclosure are not limited to use only in this context.

Overview:

In an embodiment, a system may facilitate the monitoring of vehicles, riders, and drivers. Further, the system may provide solutions for cars, vehicles, trucks motorcycles, ride-sharing car companies, taxies, and auto companies for the safety of drivers, riders and pedestrians during commutes. Further, the system may offer a safe method and environment to allow auto manufacturers to test drive new vehicles and deduct false calls and alarms. Further, the system may offer a right scale to higher standard safer decisions between humans against self-driving car technology and take a path in reaching a full safe technology at the safest environment to avoid deadly accidents and tragedies.

A driver of a vehicle may access the system through a Driver app, which may be a hands-free app and may allow the driver to use voice to interact with the app. For instance, the driver of a cab may accept trips or call a rider, open navigation, and navigate the app through hands-free gestures, such as by voice command. Further, the app may alert the driver to avoid accidents. For instance, early warning alerts or alarms may warn the driver of collision impacts and causes, such as for example other vehicles including motorcycles crossing pedestrians by using available self-driving cars deductions systems and technology.

Further, the system may monitor any bad behavior, such as unruly behavior, by riders or drivers, and may interfere, such as by providing negative ratings to the driver and/or the rider. and interfere out on the app and speakers by voice and video for a ride share.

Further, the system may allow a driver and rider to contact emergency services if required through the app.

Further, the system may monitor the driver through one or more sensors such as through a phone camera. Further, the system may generate an alarm if the driver is found not to be attentive, such as if the driver is sleepy. In an embodiment, if the driver is driving a self-driving car, the system may interface with the self-driving car and may remotely commandeer the car and drive it safely to a designated distance.

Further, the system may, through one or more connected sensors, monitor the surroundings of the vehicle through sensors installed on the vehicle. Further, the system may generate an alert if a vehicle is determined to be dangerously close to the vehicle, such as a motorcyclist driving between lanes and passing by on the right side or left side of the vehicle Further, the system may allow a driver or a rider to make a silent panic call through a silent panic button and silent in body communication. For instance, if a driver or a rider wishes to contact an emergency responder without the knowledge of one or more individuals in the vicinity of the around him or her. The silent panic button may be activated through a pre-set movement or noise, such as a number of fast breaths, coughs, or any other method that a rider and driver may choose. Further, one or more silent panic calls may be analyzed, and one or more actions of an individual leading up to or prior to the silent panic call may be analyzed. Accordingly, a silent panic call may be made to one or more emergency responders based on the analysis, and if a rider or driver is shy, or does not feel safe to use the silent panic call button. For instance, if a driver is going fast or driving under influence, the silent panic call may be placed to one or more emergency responders.

Further, the system may monitor the energy level of a driver by measuring and scanning specific items in the body, including blood pressure, heartbeat, body temperature, and so on through one or more wearable devices, such as smartwatches or fitness bands. Accordingly, a driver may be matched with a rider and a trip based on the energy level of the driver. Therefore, matching long trips may be based on a driver energy, and long trips may be given to drivers with high energy level.

Further, the system may monitor and test self-driving car technology in a safe way by analyzing one or more decisions made by self-driving cars while driving to determine false calls and wrong decisions made by the self-driving car and may improve the decision-making process.

Further, the system may incorporate existing sensors, such as cameras with one or more types of lenses, and other sensors, such as microphones, LIDAR, and so on.

Further, the system may interface with user devices, such as smartphones, and may use sensors included in the user devices such as cameras to record and monitor a vehicle. For instance, if a smartphone includes 4 cameras on a front side of the, one camera of the 4 cameras may record and monitor the eyes of a driver. The second camera may cover and monitor the rigAdvanced Technologies Group the camera may cover the middle side of the car Further, beside the self driving kit provided by selfdriving auto makers for testing, the system may include one or more external sensors positioned outside of the vehicle may, such as cameras, and other sensors such as LIDAR, SONAR, and so on. Further, the system may analyze the input received from one or more external sensors, such as images, to the camera learn and differentiate between objects, such as vehicles and pedestrians, and may aid in reducing the false calls and alarms for camera deductions Further, the system may include, and control the working of an apparatus to facilitate the reduction of blind spots while driving. The apparatus may be shaped like a cell phone holder and may include holding space for a smartphone of a user. Further, the cell phone holder may move in an opposite direction to uncover blind spots and provide a wide vision of the Advanced Technologies Group FIG. 1 is an illustration of an online platform 100 consistent Advanced Technologies Groupample, the online platform 100 to facilitate monitoring of vehicles, riders, and drivers may be hosted on a centralized server 102, such as, for example, a cloud computing service. The centralized server 102 may communicate with other network entities, such as, for example, a mobile device 106 (such as a smartphone, a laptop, a tablet computer etc.), other electronic devices 110 (such as desktop computers, server computers etc.), databases 114, sensors 116, actuators (not shown) and an apparatus 118 over a communication network 104, such as, but not limited to, the Internet. Further, users of the online platform 100 may include relevant parties such as, but not limited to, end users, drivers, riders, and administrators. Accordingly, in some instances, electronic devices operated by the one or more relevant parties may be in communication with the platform.

A user 112, such as the one or more relevant parties, may access online platform 100 through a web based software application or browser. The web based software application may be embodied as, for example, but not be limited to, a website, a web application, a desktop application, and a mobile application compatible with a computing device 700.

According to some embodiments, the online platform 100 may communicate with a system configured to facilitate monitoring of vehicles, riders, and drivers.

Further, the online platform 100 may receive input related to a vehicle from one or more driver devices. The input related to the vehicle may include sensory data, such as audio from an audio sensor or microphone, or images from one or more cameras located inside the vehicle, or outside the vehicle. Further, input related to the vehicle may include images and/or audio of the driver, and images and/or audio of surroundings of the vehicle, and so on.

Further, the online platform 100 may analyze the input related to the vehicle to detect a driver energy level, distraction, or potential obstacles. For instance, driver energy level may be detected by observing one or more of head movement, head tilt, head roll, closing of the eyes of the driver. For instance, input received from a camera of a smartphone of the driving may be analyzed to detect the head movement of the driver.

Further, the online platform 100 may facilitate commandeering of the vehicle if the driver is determined to be distracted, drowsy, or low on energy. The online platform 100 may allow the vehicle to be remotely driven to a designated area, or a safe spot. Further, the online platform 100 may a transmit notification to the one or more driver devices about or one or more obstacles. The notification may include a text message, an audible alarm accompanied by vibration, and so on, alerting the driver about the one or more obstacles.

Further, the online platform 100 may analyze one or more decisions made by drivers made while driving, such as in response to one of Advanced Technologies Groupivers. In an sentence, the analysis may include studying responses of drivers to one or more situations while driving. For instance, one or more drivers may allow an emergency responder, such as an ambulance to overtake. Accordingly, the analysis may be used in improving one or more self-driving cars, by providing responses to one or more situations arising while driving.

Figure 2:
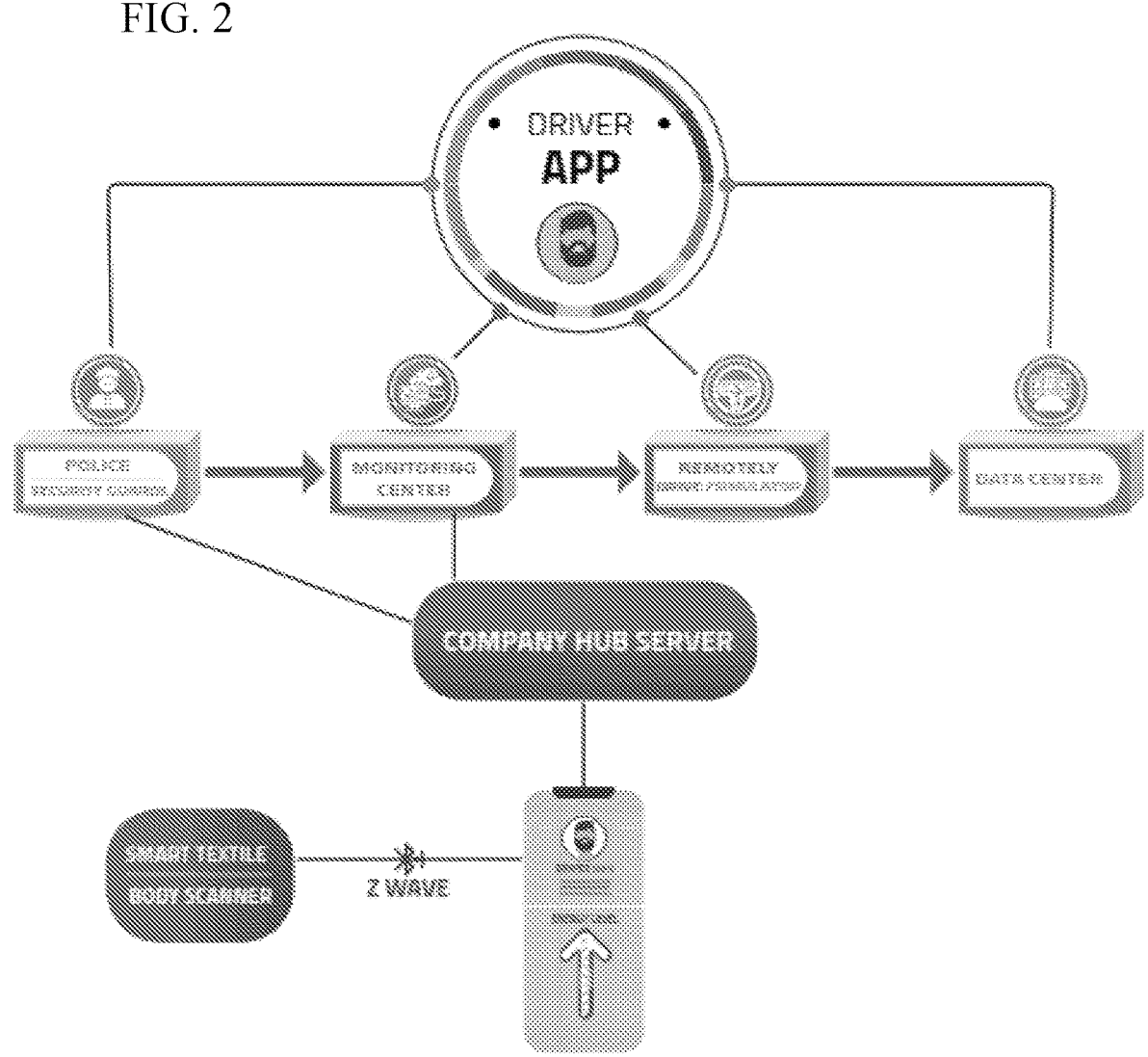
FIG. 2 shows a method to facilitate driver safety while driving a vehicle by determining driver energy level, distractions, and/or one or more obstacles, in accordance with some embodiments, illustrating drivers application and connection to each departments of monitoring center and matching center.

FIG. 2 shows a method to facilitate driver safety while driving a vehicle by determining driver energy level, distractions, and/or one or more obstacles. Further, the method may include a step of receiving, using a communication device, input related to a vehicle from one or more driver devices. The input related to the vehicle may include sensory data, such as audio from an audio sensor or microphone, or images from one or more cameras located inside the vehicle, or outside the vehicle. Further, input related to the vehicle may include images and/or audio of the driver, and images and/or audio of surroundings of the vehicle, and so on. In an instance, the input related to the vehicle may be received through an input mechanism of a driver device such as, for example, a desktop computer, laptop computer, a tablet computer, a mobile device, and a wearable device. Further, the driver device may be configured to communicate with the communication device of a server computer. Accordingly, in an instance, the input related to the vehicle input through the input mechanism may be transmitted from the driver device to the server computer. In some embodiments, the input may be automatically retrieved from one or more driver devices and/or transmitted to the server computer. For example, the driver may be provided with one or more wearable devices configured to store and transmit the corresponding input related to driver energy, such as images and/or videos. Further, upon recording or capturing of the input, the one or more wearable devices may be configured to transmit the input. Accordingly, for example, the one or more available devices may include a location sensor (e.g. GPS) configured to determine a geographical location.

Further, the method may include a step of analyzing, using a processing device, the input related to the vehicle to detect a driver energy level, distraction, or potential obstacles. Driver energy level may be detected by observing one or more of head movement, head tilt, head roll, closing of the eyes of the driver. For instance, input received from a camera of a smartphone of the driving may be analyzed to detect the head movement of the driver. For instance, if the head of the driver is determined to be displaying constant subtle movement, the driver may be determined to be attentive and may be determined to have a high energy level. Alternatively, a reduction in the head movement of the driver, along with rapid blinking and/or closing of eyes of the driver may be indicative of drowsiness, and subsequently, low drier energy level. Further, the input may be analyzed to determine potential obstacles in the path of the vehicle. For instance, sensory input received from one or more sensors in the vehicle, such as LIDAR, and/or cameras may be analyzed to determine one or more of vehicles, pedestrians and foreign objects determined to be in a projected path of the vehicle.

Further, the method may include a step of transmitting, using the communication device, a notification to the one or more driver devices about energy level, distraction, or one or more obstacles. The notification may include a text message, an audible alarm accompanied by vibration, and so on. The text message may be transmitted to a driver device, including, but not limited to a smartphone, a smartwatch, and so on. In further embodiments, if the driver is determined to be asleep, or determined to be experiencing a high degree of distraction, one or more actuators may be used to control a functioning, a movement, or both, of the vehicle. For instance, if the driver is determined to be-be drowsy, and the vehicle is a self-driving vehicle, the one or more actuators may be used to reduce the speed of the vehicle, and park the vehicle safely. Further, the vehicle may be driven to a pre-defined safe spot or location.

Figure 3:
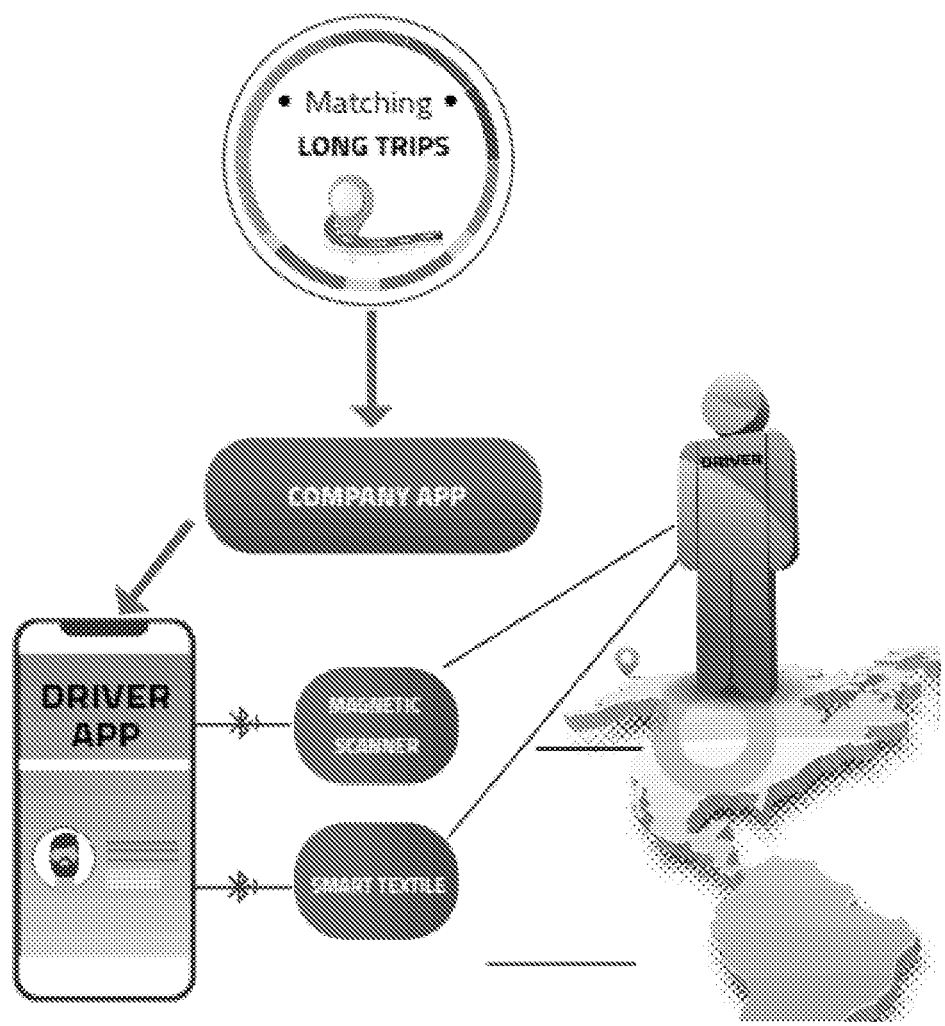
FIG. 3 shows a flowchart of a method to facilitate silent communication for a driver or a rider of a vehicle, in accordance with some embodiments.

FIG. 3 shows a flowchart of a method to facilitate silent communication for a driver or a rider of a vehicle. Accordingly, the method may include receiving, using a communication device, input related to a driver or a rider from one or more user devices. The input related to the driver or the rider may include audio, visual, gestural input received from one or more sensors capable of capturing the input. For instance, the input may include inside body silent panic alarm one or two examples more cough sounds, sounds of set of deep breaths, fast heart rates, stop for breathing for set of number of seconds or more gestures, or any combination of any of any of these. Accordingly, the input may be received from one or more sensory devices configured to record the input, such as but not limited to a camera, a microphone, an audio sensor, a smartphone, and so on. Further, in an instance, the input may correspond to one or more physiological changes in the driver or the rider, such as perspiratin, elevated heartbeat, and so on. Accordingly, the input may be received from one or more sensors configured to measure one or more physiological parameters of the driver or the rider, such as one or more wearable devices such as smartwatches, and fitness bands. Further, in an embodiment, the input may be received from one or more smart clothes and textiles worn by the driver or the rider including one or more sensors configured to measure the physiological parameters. Further, the input may also include one or more operational states of one or more user devices of the driver or the rider, such as indication of one or more received text messages, calls, and so on. Accordingly, the input may be received from the one or more user devices of the driver or the rider, such as smartphones, smartwatches, and so on.

Further, the method may include analyzing, using a processing device, the input related to the driver or the rider to detect a silent communication. The analyzing may include recognizing the input, such as recognition of one or more deep breaths, coughs, or gestures. For instance, the analyzing may including audio analysis, using one or more acoustic classifiers, image processing, and so on to recognize the received input. Further, the analyzing may include matching the recognized input against one or more preset values and/or actions to which the input may correspond. Further, the analyzing may including determining if the recognized input corresponds to an operational state to a user device of the rider or the driver. For instance, one or more number of coughs by the driver may correspond to silent communication and may be indicative of a pre-set message, such as that the rider in a vehicle being driven the driver may be unruly, or drunk, and may pose a threat while driving. Further, in an instance, the silent communication may correspond to a response to a received communication stream, such as a text message. For instance, a pre-set number of deep breaths by the may correspond to response to a phone call received by the driver, such as the message. Further, in an instance, if the input includes readings corresponding to one or more physiological changes, the analysis may include determining one or more reasons for the physiological changes. For instance, if the rider is determined to be sweating profusely, and is determined to have a high heartrate, the rider may be determined to be unable to initiate silent communication due to the driver being drunk, driving rashly, and so on.

Further, the method may include transmitting, using the communication device, a notification to one or more remote devices related to the silent communication. The notification may include a message included in the silent communication, as determined based on the analyzing. Further, the notification may be transmitted to one or more remote devices related to the silent communication, such as a remote communication center, one or more emergency responders, authorities, or one or more individuals related to the driver of the rider. For instance, if the silent communication corresponds to a driver indicating that the rider may be unruly, the notification may be transmitted to a remote communication center. Further, if the silent communication corresponds to the driver indicating responding to a text message or a phone call, the notification, including a pre-set response may be transmitted to a user device of an individual from which the text message may have been received. Further, for instance, if the silent communication corresponds to an indication that the rider may be in danger, such as due to the driver being drunk, the notification may be transmitted to one or more emergency responders. Further, in some embodiments, the silent communication may be facilitated by artificial intelligence or deep learning.

Figure 4:
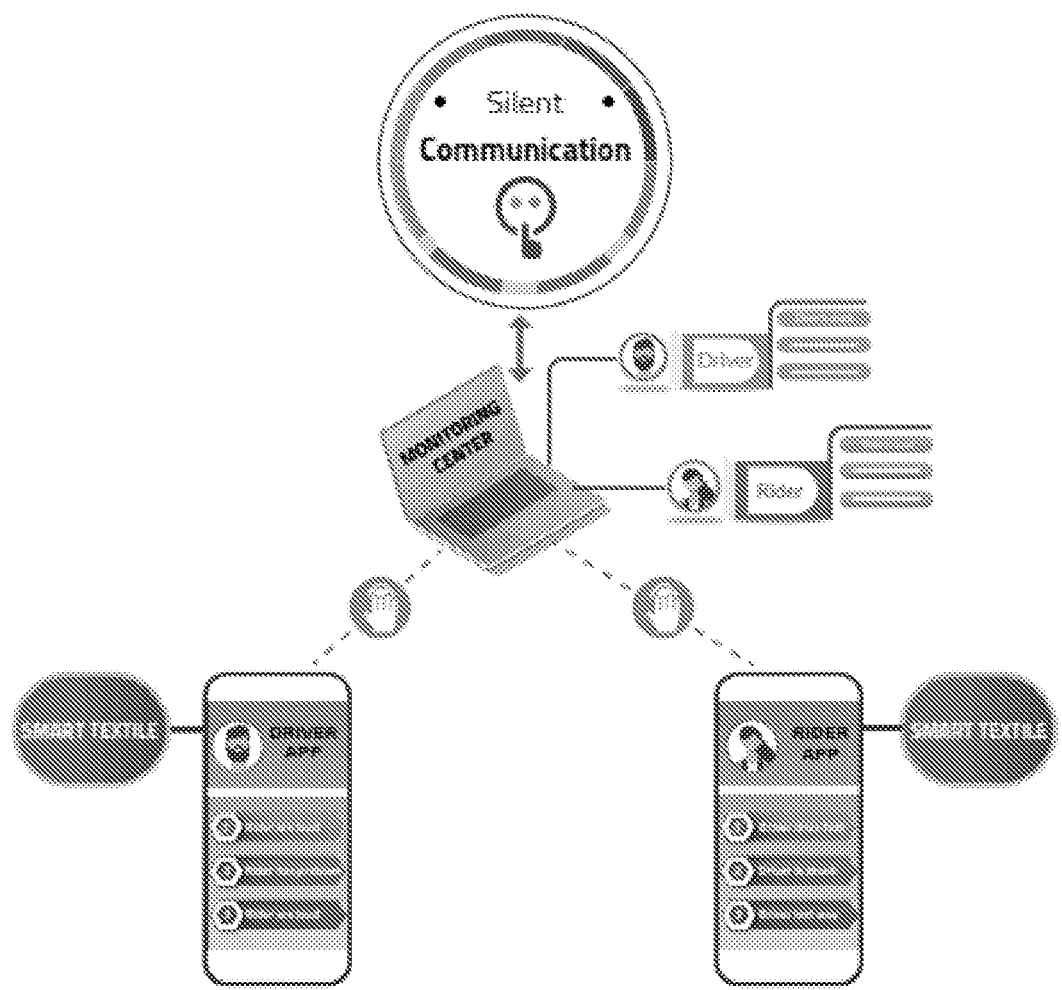
FIG. 4 shows a flowchart of a method to allow a rider to book a ride in a ride-sharing service based on an energy level of a driver, in accordance with some embodiments, in accordance with some embodiments.

FIG. 4 shows a flowchart of a method to allow a rider to book a ride in a ride-sharing service based on an energy level of a driver. Accordingly, the method may include a step of receiving, using a communication device, input related to a ride from a rider device. Input related to a ride may include location of a rider, an indication of a destination, and information related to one or more stops in the ride (if any). Further, input related to the ride may include an indication of a type of vehicle that the rider may wish to hire for the trip, such as a hatchback, a sedan, a coupe, an SUV, or even a motorcycle. Further, the input related to the ride may include a preferred payment method, and related payment details, such as cash, or details of one or more credit cards. In an instance, the input related to the ride may be received through an input mechanism of a rider device such as, for example, a desktop computer, laptop computer, a tablet computer, a mobile device, and a wearable device. Further, the rider device may be configured to communicate with the communication device of a server computer. Accordingly, in an instance, the one or more input related to the ride input through the input mechanism may be transmitted from the rider device to the server computer.

Further, the method may include receiving, using the communication device, input related to driver energy and driver availability from one or more driver devices. Input related to driver energy may include readings from one or more sensors indicating an energy level, fatigue, and/or fatigue level of a driver. For instance, input related to driver energy may include one or more of heart rate, body temperature, blood pressure, and one or more images of the face of the driver, including eyes of the driver. Further, input related to driver availability may include an indication of whether the driver may not be on a ride with one or more riders. In an instance, the input related to driver energy driver availability may be received through an input mechanism of a driver device such as, for example, a desktop computer, laptop computer, a tablet computer, a mobile device, and a wearable device. Further, the driver device may be configured to communicate with the communication device of a server computer. Accordingly, in an instance, the one or more identifiers input through the input mechanism may be transmitted from the driver device to the server computer. In some embodiments, the one or more identifiers may be automatically retrieved from one or more driver devices and/or transmitted to the server computer. For example, one or more drivers may be provided with one or more wearable devices configured to store and transmit the corresponding input related to driver energy and availability. Further, upon recording or capturing of the input, the one or more wearable devices may be configured to transmit the input. Accordingly, for example, the one or more available devices may include a location sensor (e.g. GPS) configured to determine a geographical location.

Further, the method may include a step of analyzing, using a processing device, the input related to driver energy to determine energy levels of the one or more drivers. In an embodiment, the analyzing may include comparing the input related to driver energy against one or more pre-set levels indicating driver energy. For instance, a low heart rate may indicate tiredness. Further, a high heart rate may indicate exhaustion. Further, in an instance, the analyzing may include running image processing on one or more video clips of the face of a driver and determining driver energy level and/or drowsiness. For instance, opening of the mouth multiple times for a pre-determined amount of time may indicate yawning, and low energy level. Further, closing of eyelids multiple times, for blinking, or for multiple seconds may indicate drowsiness, as determined by image processing.

Further, the method may include matching, using the processing device, the rider with a driver based on the analyzing. The rider may be matched with a driver on the basis of the energy of the driver. The rider may be matched with a driver with an energy level proportional to the energy level of the driver. For instance, if the rider may be matched with a driver of a higher energy level if the rider wishes to hire the driver and vehicle for a longer trip, so as to maintain rider and driver safety while on the trip.

Further, the method may include transmitting, using the communication device, a notification to the rider device and a matched driver device. The notification may include an indication of the match. For instance, the notification transmitted to the rider may include an indication of the driver, the vehicle, a registration number of the vehicle, a contact number of the driver, and a location of the driver. Further, the notification transmitted to the driver may include a contact number of the rider, a location of the rider, a destination of the rider, and so on.

Figure 5:
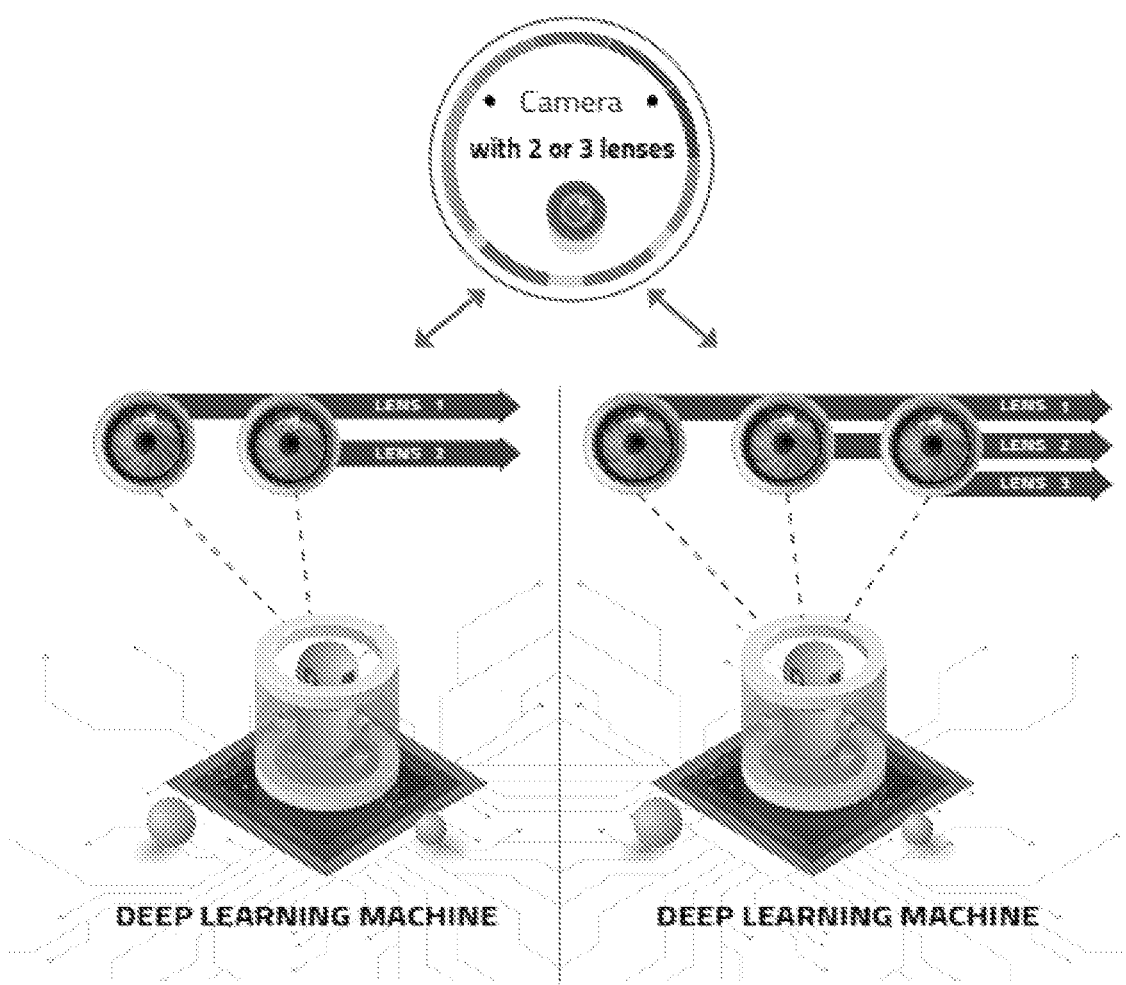
FIG. 5 shows a block diagram of a system to facilitate the monitoring of vehicles, riders, and driver, in accordance with some embodiments, illustrating a camera with one or more type of lenses connected to sensor coupled with a Deep Learning machine software connected with 3D maps.

FIG. 5 shows a block diagram of a system to facilitate the monitoring of vehicles, riders, and drivers. Further, the system may provide solutions for cars, vehicles, trucks motorcycles, ride-sharing car companies, taxies, and auto companies for the safety of drivers, riders and pedestrians during commutes. A user, such as a driver, a rider, or a system administrator may access the system through a web application, or a website, using a user device such as a smartphone, a smartwatch, a wearable device, a tablet computer, a laptop computer, a desktop computer, and so on. Further, the system may include a processing device. The processing device may be configured to perform one or more steps, such as steps described in conjunction with FIG. 2, FIG. 3, and FIG. 4. Further, the system may include a storage device. The storage device may be configured to store one or more input values received from one or more sensors, an OBD of a vehicle, or a remote server. Further, the system may include a communicate device configured to communicate with one or more external devices, such as a remote server, the OBD of the vehicle, and one or more sensory devices and one or more user devices of a user of the system over a communication network including, but not limited to mobile network, Bluetooth, W-Fi, and so on. Further, in an instance, the system may communicate with, and control the working of an apparatus to facilitate the reduction of blind spots while driving, such as the apparatus described in conjunction with FIG. 6.

Figure 6:
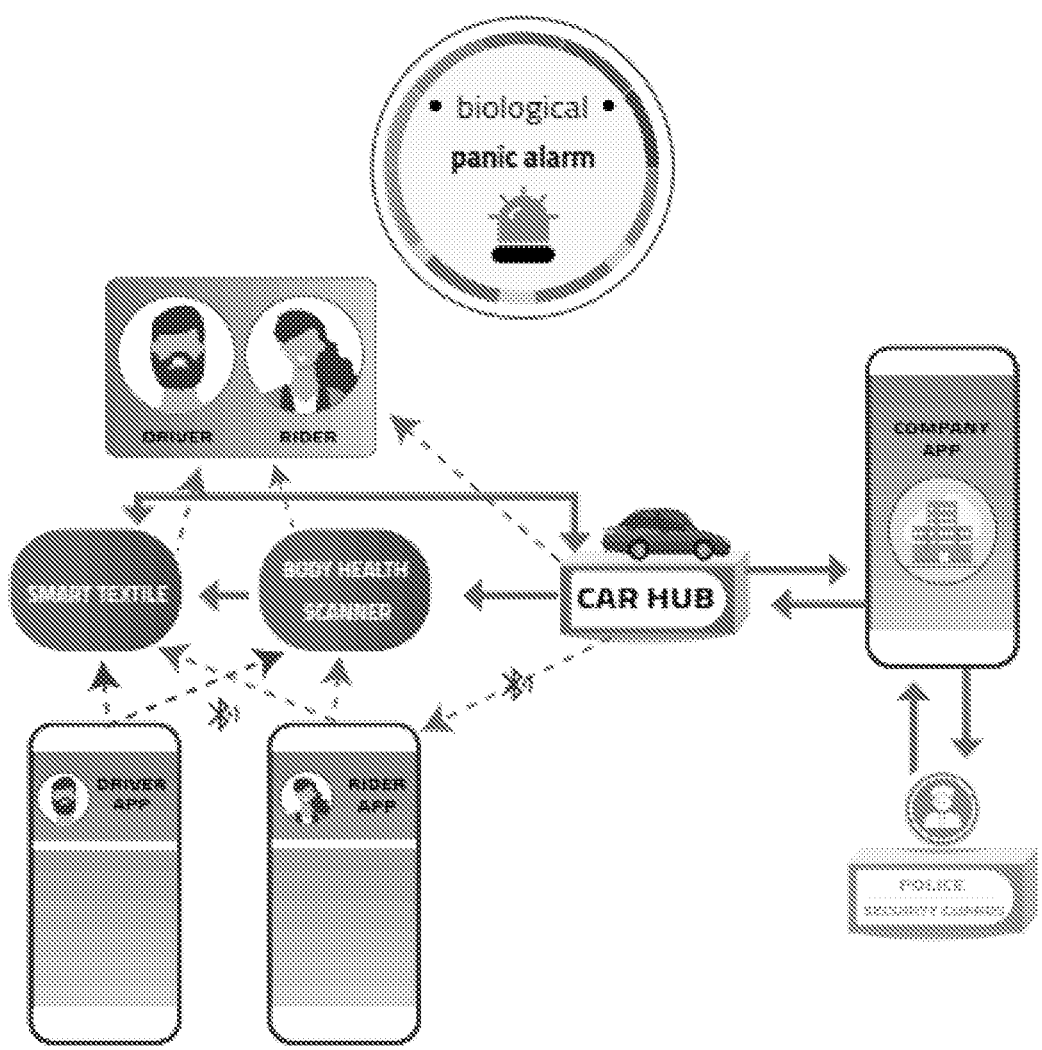
FIG. 6 shows an apparatus to facilitate the reduction of blind spots while driving, in accordance with some embodiments, illustrating a chart of Silnet biological panic alarm where the driver and rider can transmit in case of danger so it comes from inside their bodies.

FIG. 6 shows an apparatus to facilitate the reduction of blind spots while driving. The apparatus may be shaped like a cell phone holder and may include holding space for a smartphone of a user. Further, the apparatus may move in an opposite direction to uncover blind spots and provide a wide vision of the front windshield and the street. For instance, if a vehicle is moving uphill the apparatus with a smartphone may move downwards so that the driver may receive a clear vision, and may be able to view the complete windshield. In an instance, the apparatus may include sensors such as a gyroscope and an accelerometer, which may aid the apparatus in moving in a direction opposite to the movement of the vehicle. Further, in an instance, the apparatus may be in communication with a system to facilitate the monitoring of vehicles, riders, and drivers, such as the system described in FIG. 5, and may be controlled by the system. Further, the manner in which the holder may need to be moved may be learned by deep learning or machine learning.

Figure 7:
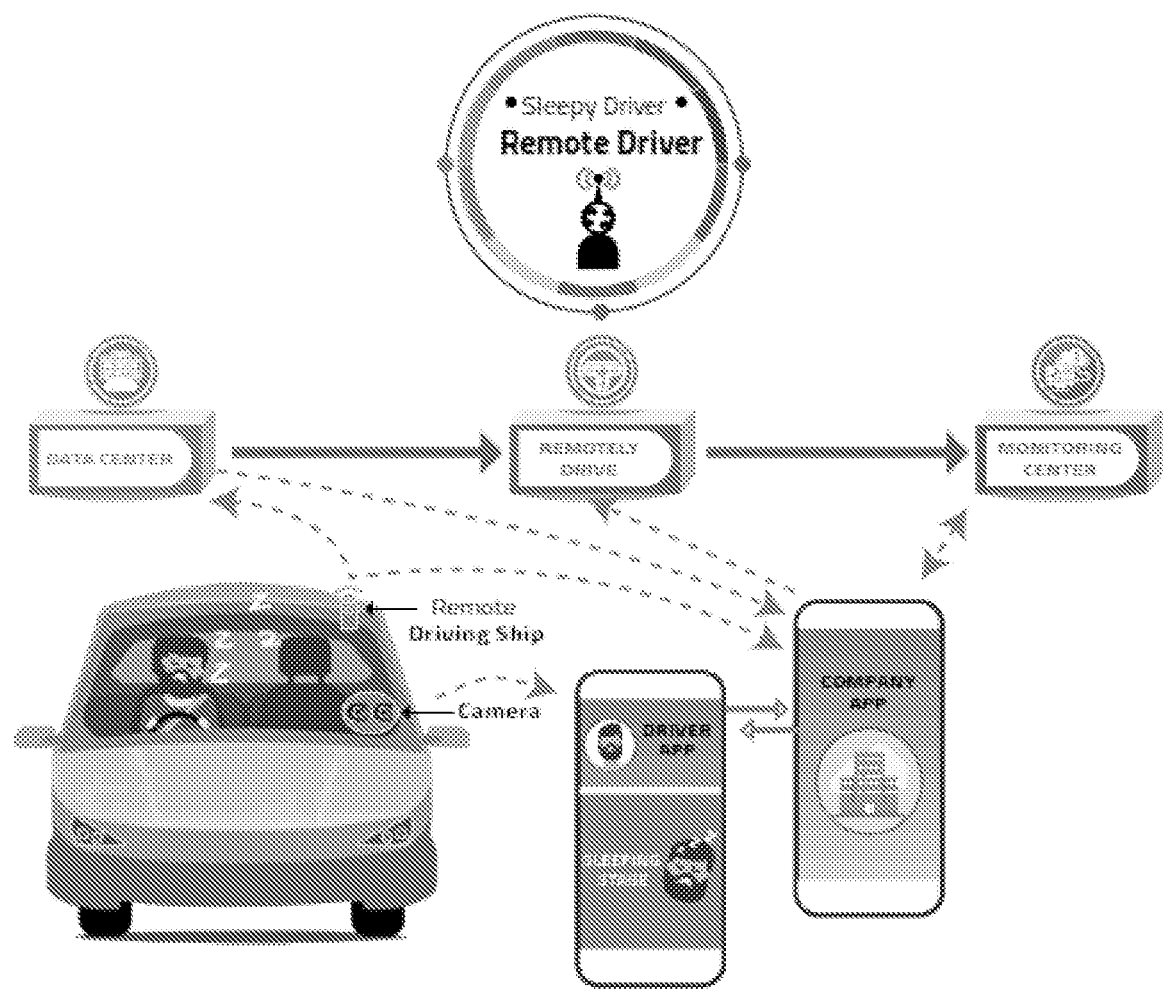
FIG. 7 is a block diagram of a computing device for implementing the methods disclosed herein, in accordance with some embodiments, illustrating the monitoring of sleepy drivers and remotely driving the sleepy drivers from a remote monitoring center.
Figure 8:
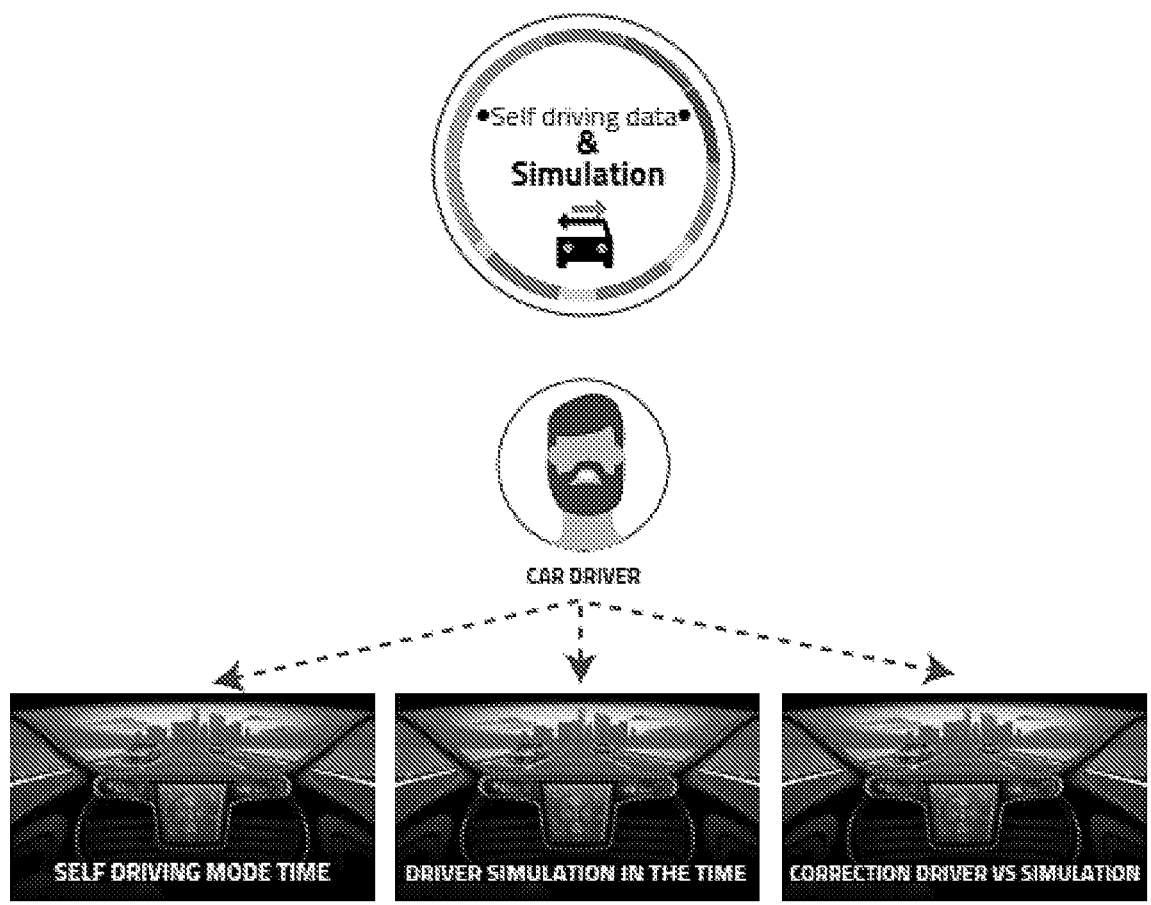
FIG. 8 is a diagram showing a live simulation to virtual mode of a self-driving car for each driver of the present invention.
Figure 9:
FIG. 9 is health scanners and smart textile we use to scan driver energy, to use for Silnet communications and for sending biological-silent panic alarm from inside human bodies.
Figure 9:
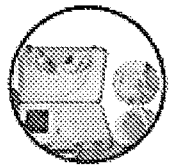
Figure 9:
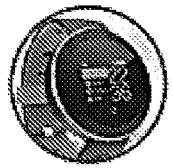
Figure 9:
Figure 9:

With reference to FIG. 7, a system consistent with an embodiment of the disclosure may include a computing device or cloud service, such as computing device 700. In a basic configuration, computing device 700 may include at least one processing unit 702 and a system memory 704. Depending on the configuration and type of computing device, system memory 704 may comprise, but is not limited to, volatile (e.g. random-access memory (RAM)), non-volatile (e.g. read-only memory (ROM)), flash memory, or any combination. System memory 704 may include operating system 705, one or more programming modules 706, and may include a program data 707. Operating system 705, for example, may be suitable for controlling computing device 700's operation. In one embodiment, programming modules 706 may include image-processing module, machine learning module and/or image classifying module. Furthermore, embodiments of the disclosure may be practiced in conjunction with a graphics library, other operating systems, or any other application program and is not limited to any particular application or system. This basic configuration is illustrated in FIG. 7 by those components within a dashed line 708.

Computing device 700 may have additional features or functionality. For example, computing device 700 may also include additional data storage devices (removable and/or non-removable) such as, for example, magnetic disks, optical disks, or tape. Such additional storage is illustrated in FIG. 7 by a removable storage 709 and a non-removable storage 710. Computer storage media may include volatile and nonvolatile, removable and non-removable media implemented in any method or technology for storage of information, such as computer-readable instructions, data structures, program modules, or other data. System memory 704, removable storage 709, and non-removable storage 710 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 700. Any such computer storage media may be part of device 700. Computing device 700 may also have input device(s) 712 such as a keyboard, a mouse, a pen, a sound input device, a touch input device, a location sensor, a camera, a biometric sensor, etc. Output device(s) 714 such as a display, speakers, a printer, etc. may also be included. The aforementioned devices are examples and others may be used.

Computing device 700 may also contain a communication connection 716 that may allow device 700 to communicate with other computing devices 718, such as over a network in a distributed computing environment, for example, an intranet or the Internet. Communication connection 716 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 704, including operating system 705. While executing on processing unit 702, programming modules 706 (e.g., application 720 such as a media player) may perform processes including, for example, one or more stages of methods, algorithms, systems, applications, servers, databases as described above. The aforementioned process is an example, and processing unit 702 may perform other processes. Other programming modules that may be used in accordance with embodiments of the present disclosure may include sound encoding/decoding applications, machine learning application, acoustic classifiers etc.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general purpose graphics processor-based systems, multiprocessor systems, microprocessor-based or programmable consumer electronics, application specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

What is claimed is:

1. A method for silent unheard communications between a driver/rider and a monitoring center through sending text messages via a cell phone without the driver/rider touching the cell phone, the method comprising: preset text messages stored as a set of numbers on a driver/rider app, said driver/rider app connected to a smart wearable textile that has a biometric access control sensor built in the smart wearable textile through an internet protocol relay so if the driver/rider touches the biometric sensor once, the relay sends a first preset massage to the monitoring center and if the driver/rider touches the sensors twice, immediately right away after a first touch, then a second preset message is texted to the monitoring center.

* * * * *